United States Patent
Stoltenberg et al.

[11] Patent Number: 6,096,039
[45] Date of Patent: Aug. 1, 2000

[54] MEANS FOR INTERCONNECTING TWO SPACED ELONGATED RODS OF A HUMAN SPINE IMPLANT

[75] Inventors: Ingo Stoltenberg, Probsteierhagen; Bernd Robioneck, Preetz, both of Germany

[73] Assignee: Howmedica GmbH, Germany

[21] Appl. No.: 09/311,189

[22] Filed: May 12, 1999

[30] Foreign Application Priority Data

May 13, 1998 [DE] Germany .................. 298 08 593 U

[51] Int. Cl.⁷ .................................................. A61B 17/58
[52] U.S. Cl. ................................................ 606/61; 606/72
[58] Field of Search .............................. 606/61, 69, 72, 606/73, 74

[56] References Cited

U.S. PATENT DOCUMENTS

| | | | |
|---|---|---|---|
| 4,257,409 | 3/1981 | Bacal et al. ............................. | 128/69 |
| 4,274,401 | 6/1981 | Miskew ..................................... | 606/61 |
| 4,567,884 | 2/1986 | Edwards ................................... | 128/69 |
| 4,611,582 | 9/1986 | Duff ......................................... | 606/61 |
| 5,034,011 | 7/1991 | Howland ................................... | 606/61 |
| 5,102,412 | 4/1992 | Rogozinski ............................... | 606/61 |
| 5,147,360 | 9/1992 | Dubousset ................................. | 606/61 |
| 5,154,718 | 10/1992 | Cozad et al. ............................. | 606/61 |
| 5,439,463 | 8/1995 | Lin ........................................... | 606/61 |
| 5,601,552 | 2/1997 | Cotrel ....................................... | 606/61 |
| 5,620,444 | 4/1997 | Assaker .................................... | 606/61 |
| 5,651,789 | 7/1997 | Cotrel et al. ............................. | 606/61 |
| 5,743,911 | 4/1998 | Cotrel ....................................... | 606/61 |
| 5,800,548 | 9/1998 | Martin et al. ............................. | 623/17 |
| 5,899,903 | 5/1999 | Cotrel ....................................... | 606/61 |
| 5,928,231 | 7/1999 | Klein et al. ............................... | 606/61 |

FOREIGN PATENT DOCUMENTS 0 446 092 B1   7/1995   European Pat. Off. .
2 645 427 A1  10/1990   France .

*Primary Examiner*—Michael Buiz
*Assistant Examiner*—Dapha Shai
*Attorney, Agent, or Firm*—Lerner, David, Littenberg, Krumholz & Mentlik, LLP

[57] ABSTRACT

A means for the interconnection of two spaced elongated rods of a human spine implant, comprising a hook having a mouth and being adapted to partially grip around a first elongated rod, a transverse bar connected to the hook and gripping means adapted to be connected to the second elongated rod and to be attached to the transverse bar, whereby transverse bar and hook arm interconnected through a joint, the joint having joint portions which are adapted to be pivoted between a release position and a locking position, in that further locking means are provided which inhibit a pivoting of the joint portions of the hook to the release position and in that the joint portion connected to the transverse bar is structured such that in the release position the hook with its mouth can be freely placed onto the elongated rod while in the locking position the rod is locked within the mouth.

12 Claims, 3 Drawing Sheets

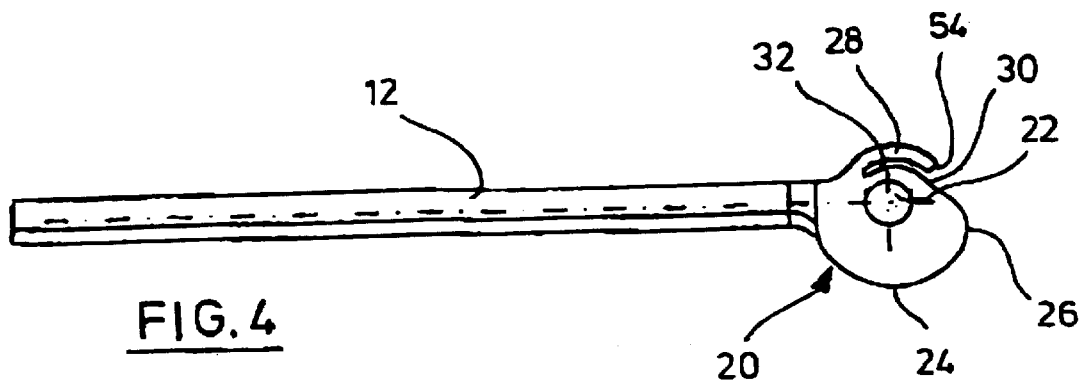
FIG. 4
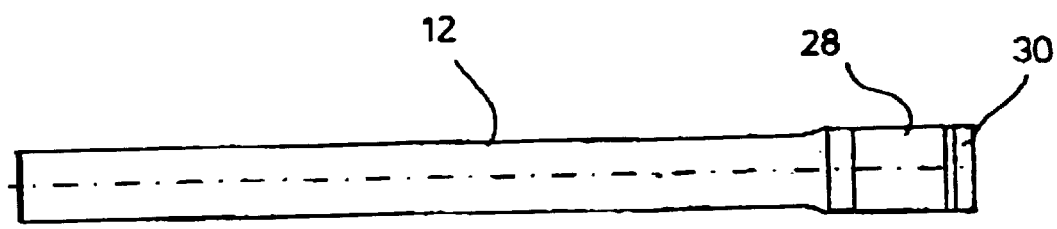
FIG. 5
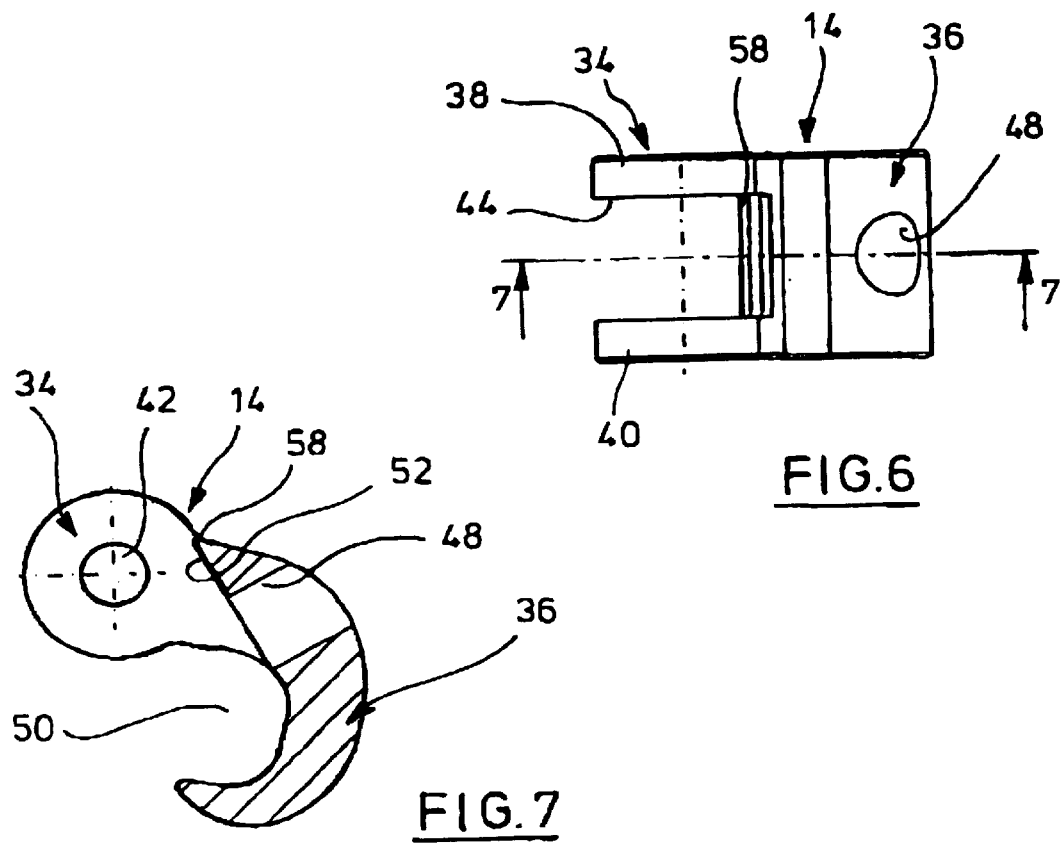
FIG. 6
FIG. 7

MEANS FOR INTERCONNECTING TWO SPACED ELONGATED RODS OF A HUMAN SPINE IMPLANT

The invention refers to means for the interconnection of two spaced elongated rods of a human spine implant.

For the stabilization, reposition, distraction or the like of vertebras of a human spine it is known to apply suitable implants. Such implants normally include pedicle screws which are adapted to be screwed into the pedicle of the vertebras. It is known to interconnect vertebras through such pedicle screws and further suitable means, e.g. elongated rods which are attached to the pedicle screws by suitable fastening means. Frequently, there is the necessity that such elongated rods which normally are extended parallel to each other in accordance with the arrangement of the pedicle screws are to be interconnected through at least one transverse bar. Also to this purpose suitable means are known. The known devices have the disadvantage that the surgeon needs much time to install the connection means. The space between the rods and their position differ significantly, and the accessiblity for the application of the interconnection means is restricted.

Object of the invention is to provide a means for the interconnection of two spaced elongated rods of a human spine implant which is simply structured and allows a quick installation.

In the means according to the invention a transverse bar forms a joint with a hook. The hook is designed such that it may embrace the elongated rod through its mouth in order to exert a transverse force onto the elongated rod. It is essential to the invention that the hook may attain different positions relative the transverse bar. In a release position the mouth of the hook may freely accommodate an elongated rod and allow the removal thereof. If, however, a relative pivoting of rod and hook into the locking position is effected, it inhibits a release of the rod from the hook. In the most simple manner this can be achieved in that the entrance area of the mouth is narrowed. In order to prevent the hook from pivoting into the release position, locking means are provided which become effective if the hook is pivoted into the locking position.

The connection of such a means to an elongated rod thus take place in the manner that hook and transverse bar have a predetermined angle relative to each other so that the hook may be conveniently placed onto the elongated rod. Thereafter the elongated rod is pivoted relative to the hook to an extent that the locking position is reached. Preferably, the structure of the link of the joint associated with the bar is such that the elongated rod is clamped within the mouth of the hook more or less.

By means of a suitable gripping means which is connected to the other end of the transverse bar a connection with a second elongated rod can be made.

The linking of the transverse bar to the hook is preferably such that in the locking position the tensional force at the hook is approximately axially transferred to the transverse bar. By this, only a relatively small force is exerted onto the locking means when the transverse bar is set under tension.

According to an embodiment of the invention the narrowing of the entrance portion of the mouth of the look or rowing of the elongated rod in the mouth, respectively, can be achieved in that the joint portion associated with the transverse bar has an eccentric surface which faces the mouth of the hook.

According to another embodiment of the invention the locking means can include a deformable extension attached to the joint portion connected with the transverse bar. The extension cooperates with an edge of the hook when the hook is pivoted into the locking position. Preferably, the locking extension is formed by an arcuate segment of the joint portion which is formed by an arcuate slot in the joint portion.

According to a further embodiment of the invention the mouth portion of the hook has a throughgoing opening which in the locking position is located approximately at the level of the locking means. By this, a tool can be inserted to disengage the locking means or the locking extension, respectively from the edge whereby the hook thus can be pivoted into the release position.

Different structural embodiments are conceivable for the design of the gripping means at the other end of the transverse bar. Above all, it is essential that the gripping means are slidably supported by the bar in order to achieve an adaptation to the space of the elongated rods. According to an embodiment of the invention, this gripping means is also formed by a hook having a support portion which includes a passage for the extension of the transverse bar therethrough as well as a axial bore for the accommodation of a set screw. In order to simply attach this hook to the transverse bar, the passage is open to the free end of the support portion. By this, the transverse bar can be readily inserted into the support portion. Thereafter the set screw, preferably a headless screw, is threaded into the threaded bore in order to fix the hook onto the transverse bar.

The thread of the support portion preferably has a saw tooth shape such that the steeper flank of the thread faces the mouth portion. By this, it is prevented that upon load the set screw is released from the fork-shaped head in that the leg portions are bent away from each other. By means of such a thread substantially only tensional forces are exerted on the leg portions which do not result in a bending thereof.

Embodiments of the invention are subsequently explained along accompanying drawings.

FIG. 4 is a side view of a transverse bar with a joint portion of the means of FIG. 1.

FIG. 5 is a plan view of the portion of FIG. 4.

FIG. 6 shows a plan view of the pivotable hook of the means of FIG. 1.

FIG. 7 is a section through the means of FIG. 6 along line 7—7.

Figure 1:
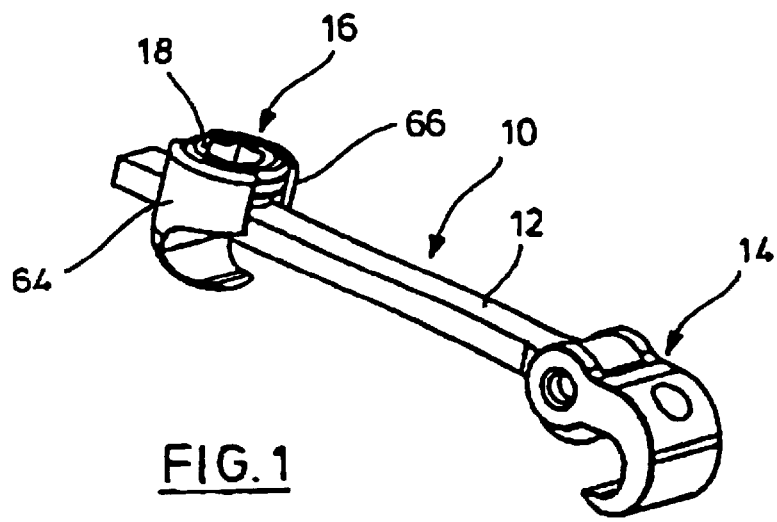
FIG. 1 is a perspective view of a means according to the invention.

The means 10 shown in FIG. 1 include a transverse bar 12 substantially rectangular in cross section, a first hook 14 and a second hook 16. The first hook 14 is connected to the transverse bar 12 through a joint This is explained in more detail hereinafter. The second hook 16 is rigidly attached to transverse bar 12. It includes a passage to be described herebelow for the accommodation of the transverse bar 12 which by means of a set screw 18 is fixed within the hook 16.

The structure of hook 14 and of the joint with the transverse bar 12 can be more clearly seen in the FIGS. 4 to 7. As can be seen in FIG. 4, a disc-shaped joint portion 20 is provided having a throughbore 22. In the lower area the circumferential surface 24 of the joint portion 20 is circular while at 26 an eccentric bulge is provided which in the direction of an arcuate segment 28 is provided with indentation 30. The arcuate segment 28 is formed by an arcuate slot 32.

Hook 14 has a support portion 34 and a mouth portion 36. The support portion 34 is fork-shaped and has two spaced legs 38, 40 which both have a throughbore 42. The leg portions 39, 40 form a recess 44 adapted to accommodate the disc-shaped joint portion 20, with the throughbores 42, 22 being aligned for the accommodation of a joint pin (not shown). The hook portion 36 has a throughbore 48 which is open to recess 44 and extends into the mouth 50 of hook 40. A surface 52 is formed by the leg portions 38, 40 of the support portion at the side facing the recess 44. The surface is located on the outer side of the arcuate segment 28 after the assembly of the joint portions. In the assembling position the hook 14 is pivoted upwardly if compared with FIGS. 1 and 2. If hook 14 is pivoted relative to transverse bar 12 into the position shown in FIGS. 1 and 2 the free end 54 of segment 28 engages behind a shoulder 58 formed by surface 52 and thus locks hook 14 in such a manner that it cannot pivot back. The arrangement of the surface 52 is such that upon rotation of the hook segment 28 is slightly deformed radially inwardly so that it subsequently may engage edge 58.

In other words, when hook portion 36 is mounted on joint portion 20, shown in FIG. 4, via a pivot pin with surface 52 located above arcuate segment 28 clockwise rotation of portion 36 depresses segment 28. When tip 58 passes arcuate segment 28 it springs back outwardly thus, acting as a stop preventing hook 36 from rotating counterclockwise. In order to unlock the hook 36 from around rod 60 a tool is inserted between arms 34 and 40 to depress arcuate segment 28. This allows counterclockwise rotation of edge 58 over segment 28 and allows removal of rod 60.

In order to accomplish this, surface 52 must be at a distance from the pivot axis greater than slot 32, but less than the outer surface of segment 28.

Figure 2:
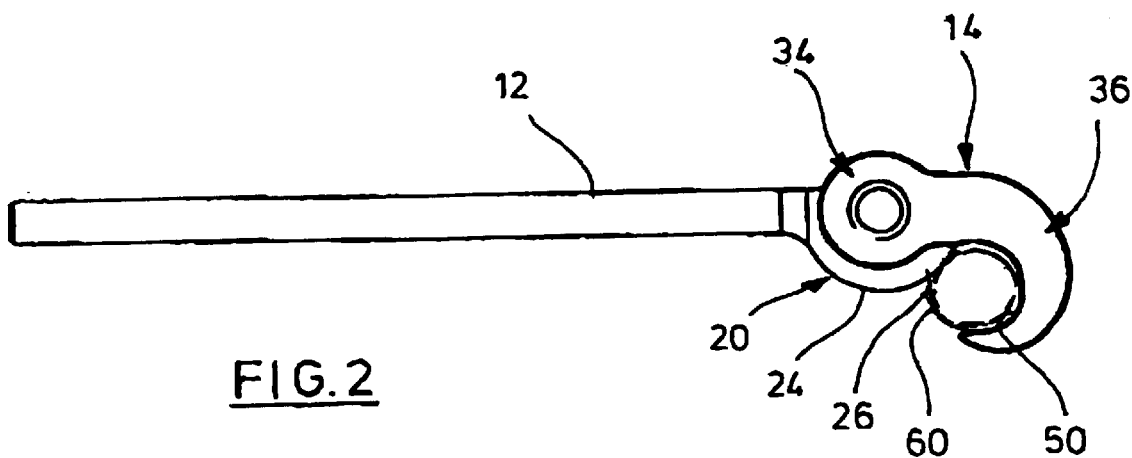
FIG. 2 is a side view of a portion of the means of FIG. 1.
Figure 3:
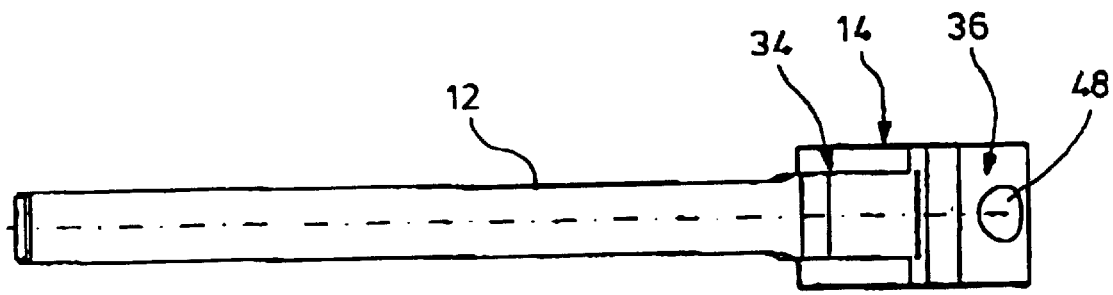
FIG. 3 is a plan view on the portion of FIG. 2.

If prior to this operation a rod is inserted into mouth 50 of the hook as shown at 60 in FIG. 2 and afterwards the hook is pivoted into the position shown in FIGS. 1 and 2 rod 60 is clamped within mouth 50 of hook 14 as the eccentric portion 26 restricts or narrows the entrance area of the mouth. As already mentioned, the hook cannot be turned or pivoted back. Thus, rod 60 is safely attached to mouth 50.

Figure 8:
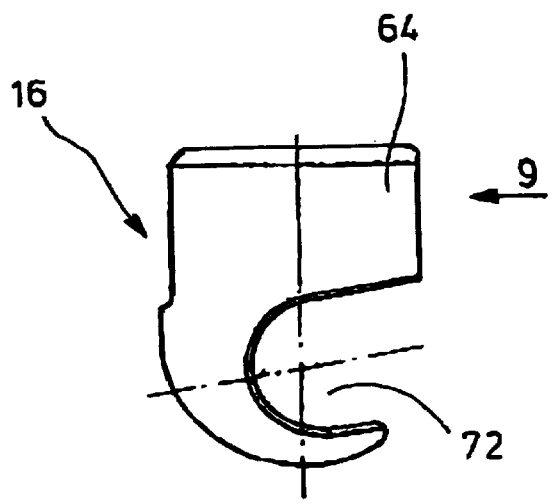
FIG. 8 is a side view of means of FIG. 1.
Figure 9:
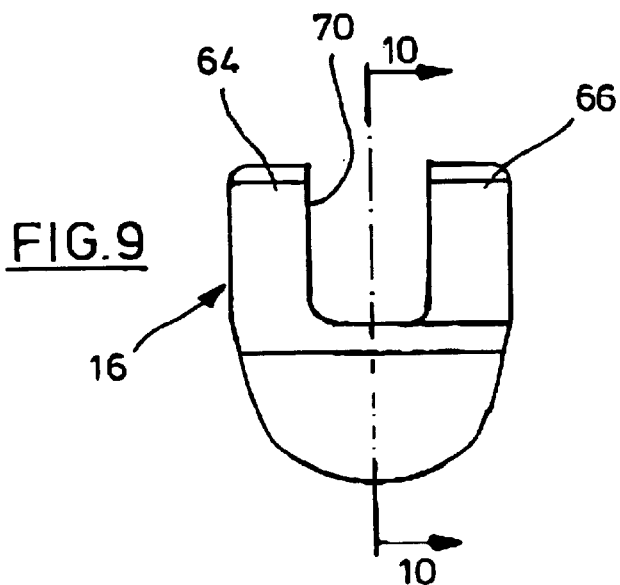
FIG. 9 is a side view of the hook of FIG. 8 in the direction of arrow 9.
Figure 10:
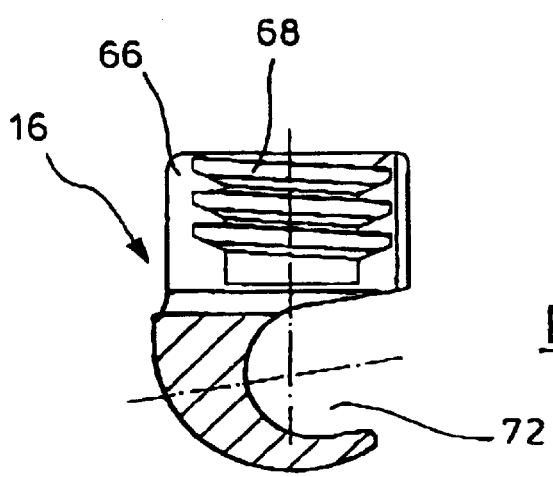
FIG. 10 is a cross section through the hook of FIG. 9 along line 10—10.

In FIGS. 8 to 10 a second hook 16 is shown in detail. As can be seen in FIG. 1, hook 16 has two arcuate support portions 64, 66. The support portions 64, 66 have threaded portions, one of the threaded portion is shown at 68 in FIG. 10. A passage 70 is provided between the support portions 64, 66. The passage 70 is opened to the free end of the support portion. The passage is adapted to accommodate the transverse bar 12 as shown in FIG. 1. A set screw 18 is threaded into the threaded portions 68 in order to fix bar 12 to the hook 16. The hook mouth 72 accommodates a second elongated rod not shown without fixing the rod axially. The threaded portions 68 are shaped such that one flank of the threads extends substantially perpendicular to the axis, i.e. the flank facing mouth 72. Possibly occurring tensional forces at mouth 22 thus are only transferred as tensional forces to portions 64, 66. Thus, the portions 64, 66 are prevented from being bent away from each other which otherwise may affect the threaded engagement of the set screw 18.

We claim:

1. A device for interconnecting a first and a second spaced elongated rods of a human spine implant, comprising a hook having a mouth and being adapted to partially grip around the first elongated rod, a transverse bar connected to the hook at a first end and connected to the second elongated rod at a second end, said transverse bar and hook are interconnected through a joint having at least two joint portions which are pivoted between a release position and a locking position, a first of said joint portions including said hook, a lock is provided which prevents a pivoting of the at least two joint portions of the hook with respect to each other to the release position a second joint portion of said at least two portions being connected to the transverse bar and structured such that in the release position the hook with its mouth can be freely placed onto the first elongated rod while when pivoted to the locking position the rod is locked within the mouth.

2. The device of claim 1, wherein the second joint portion associated with the transverse bar has an eccentric surface facing the mouth of the hook.

3. The device of claim 1 or 2, wherein the second joint portion associated with the transverse bar has a deformable locking portion, an edge of the first joint portion may snap behind said locking portion when the hook is pivoted into the locking position.

4. The device of claim 3, wherein the second joint portion is arcuate in shape and the locking portion is shaped as an arcuate segment formed by an arcuate slot cut in said second joint portion.

5. The device of claim 4, wherein the first joint portion includes a mouth portion formed in said hook having a shoulder which in the locking position of the hook is located approximately at the level of said arcuate segment.

6. The device of claim 1, wherein the second end of said rod includes a clamp having a hook with a support portion thereof including a passage for the accommmodation of the transverse bar and an axial threaded bore for the accommodation of a set screw which cooperates with the transverse bar within the passage.

7. The device of claim 6, wherein the passage is open to the free end of the support portion in order to facilitate the insertion of the transverse bar.

8. The device of claim 6 or 7, wherein the thread of the threaded bore has saw tooth-shaped flanks such that the steeper flanks face the hook portion.

9. A connector for connecting two rods attached to a human spine comprising;

a transverse bar having an arcuate pivot element formed on a first end thereof, said pivot element having an outer arcuate surface with a locking element formed thereon selectively operable from a first locking position to a second release position;

a joint element having a hook formed thereon, said hook defining a mouth, the joint element pivotally coupled to said pivot element for rotation with respect thereto about a pivot axis to move said mouth from an open to a close position:

said outer arcuate surface of said pivot element has an eccentric shape such that rotation of said joint element from said open position to said closed about said pivot axis decreases the distance between said outer surface of said pivot element and an inner surface of said mouth on said joint element; and said arcuate pivot element includes a circumferential slot spaced radially inwardly of said outer arcuate surface to define a radially deflectible spring segment forming part of said outer surface.

10. The connector as set forth in claim 9 wherein said joint element has a shoulder formed thereon and located at a distance from said pivot axis greater than said slot but less than the outer arcuate surface of said spring segment so that upon rotatio of said joint element from said open to said closed position said shoulder deflects said spring segment radially inwardly.

11. The connector as set forth in claim 12 wherein said joint element has a pair of bifurcated arms for capturing said pivot element therebetween with said shoulder extending between said arms.

12. The connector as set forth in claim 9 wherein said transverse bar has a hook element slideably mounted thereon adjacent a second end thereof for movement in a direction along a longitudinal axis of the bar.

* * * * *

UNITED STATES PATENT AND TRADEMARK OFFICE
CERTIFICATE OF CORRECTION

PATENT NO. : 6,096,039
DATED : August 1, 2000
INVENTOR(S) : Stoltenberg et al.

It is certified that error appears in the above-identified patent and that said Letters Patent is hereby corrected as shown below:

In the Abstract:
line 7, "arm" should read -- are --.

Column 1, line 61, "look" should read -- hook --.
Column 2, line 22, "a" should read -- an --.
Column 3, line 49, "portion" should read -- portions --.
Column 4, line 10, after "position" insert -- , --.
Column 4, line 57, "close" should read -- closed --.
Column 5, line 5, "rotatio" should read -- rotation --.

Signed and Sealed this

Fifteenth Day of May, 2001

Attest:

NICHOLAS P. GODICI

Attesting Officer

Acting Director of the United States Patent and Trademark Office